United States Patent [19]

Okamoto et al.

[11] 3,944,622
[45] Mar. 16, 1976

[54] METHOD FOR PRODUCING KETONES

[75] Inventors: Takehiko Okamoto; Tamihiro Ohashi, both of Ichihara; Isao Koga, Yokohama, all of Japan

[73] Assignee: Chisso Corporation, Osaka, Japan

[22] Filed: Sept. 12, 1973

[21] Appl. No.: 396,660

[52] U.S. Cl............................ 260/593 R; 252/461
[51] Int. Cl.² ............................................. C07C 45/00
[58] Field of Search................ 260/590, 592, 593 R

[56] References Cited
UNITED STATES PATENTS

| | | | |
|---|---|---|---|
| 2,549,508 | 4/1951 | Mottern | 260/593 R |
| 3,453,331 | 7/1969 | Hargis et al. | 260/593 R |
| 3,466,334 | 9/1969 | Young et al. | 260/593 R |

OTHER PUBLICATIONS

Masahiro et al., Chem. Abs., 78: 57765t.

*Primary Examiner*—Bernard Helfin
*Assistant Examiner*—James H. Reamer
*Attorney, Agent, or Firm*—Fred Philpitt

[57] ABSTRACT

Ketones are prepared with a high yield and a prolonged catalyst life, by reacting an aldehyde selected from the group consisting of straight chain or branched chain aliphatic aldehydes having a carbon number of 4–10 (inclusive) and aromatic aldehydes represented by the general formula of

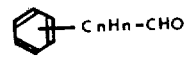

wherein $n$ is 0–5 with a monocarboxylic acid selected from the group consisting of acetic acid and propionic acid, at a temperature of 200°–600°C, in the presence of a catalyst of zirconium oxide alone or a mixture of zirconium oxide and at least one kind of the metal oxide selected from the group consisting of alkali metal oxides and alkaline earth metal oxides.

11 Claims, No Drawings

METHOD FOR PRODUCING KETONES

DESCRIPTION OF THE INVENTION

This invention relates to a novel method for producing ketones from a mixture of an aldehyde and a carboxylic acid by the use of a solid catalyst. More particularly, it relates to a method for producing ketones by contacting a mixture of an aldehyde and a carboxylic acid with a solid catalyst of zirconium oxide alone or a mixture of zirconium oxide and at least one kind of the metal oxide selected from the group consisting of alkali metal oxides and alkaline earth oxides to form a corresponding ketone.

We previously discovered a method for producing ketones from aldehydes in a commercially satisfactory yield, by using a zirconium oxide catalyst alone or a catalyst in which an alkali metal oxide or an alkaline earth metal oxide is added to zirconium oxide.

However, this method still has a drawback in that, when lower aliphatic aldehydes such as acetaldehyde, propionaldehyde, etc. are employed, remarkable degradation of catalyst occurs, which results in the necessity of very frequent repetitions of catalyst regeneration making the process cumbersome.

After strenuous studies, we have found that when lower aliphatic carboxylic acids such as acetic acid, propionic acid, etc. are employed together with lower aliphatic aldehydes in place of lower aliphatic aldehydes alone, the catalyst life is extremely prolonged and also the yield of ketones is improved, and thus have completed the present invention.

The present invention resides in a method for producing ketones which comprises reacting an aldehyde selected from the group consisting of straight or branched chain aliphatic aldehydes having 4 to 10 carbon atoms and aromatic aldehydes expressed by the general formula,

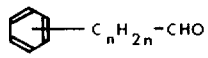

wherein $n$ is an integer of 0 to 5, with a monocarboxylic acid selected from the group consisting of acetic acid and propionic acid, at a temperature of 200° to 600°C, in the presence of a catalyst consisting of zirconium oxide alone or a mixture of 99.5–90% by weight of zirconium oxide and 0.5–10% by weight of at least one kind of the metal oxide selected from the group consisting of alkali metal oxides and alkaline earth metal oxides.

The preparation of the catalyst used in the present invention can be illustrated as follows: Water-soluble salts such as nitrate, sulfate, phosphate, chloride, organic acid salts, etc. of zirconium, alkali metals and alkaline earth metals, are mainly used as starting materials. An alkaline substance such as aqueous ammonia or the like is added to an aqueous solution of a salt of zirconium alone, or an aqueous solution of a mixture of the above-mentioned starting materials in which they are mixed so as to give a catalyst composition aimed, dropwise with stirring to precipitate zirconium hydroxide or coprecipitate the hydroxides corresponding to the above-mentioned materials, followed by filtration, water washing, drying and calcination at 200°–1000°C, preferably 400°–800°C, for activation.

Further, as for the introduction of alkali metal oxides to the catalyst system, it is also possible to add an aqueous solution of caustic alkali as a precipitant to the aqueous solution of a zirconium salt.

Furthermore, the following method is also effective: Zirconium oxide or hydroxide is dipped in an aqueous solution of water-soluble salts of alkali metals or alkaline earth metals, followed by drying and calcination. Namely, these oxides are supported on zirconium oxide.

Still further, it is also possible to use a catalyst obtained by impregnating a carrier such as activated carbon, activated alumina, silica, etc., with a mixed aqueous solution of water-soluble salts of zirconium and alkali metals or alkaline earth metals.

As for the alkali metals to be used for the present invention, Li, Na, K, Rb and Cs are illustrated, and as for the alkaline earth metals therefor, Be, Mg, Ca, Sr and Ba are illustrated. The oxides of these metals can be used in an amount of 0.5–95% by weight based upon the weight of the total catalyst composition including zirconium oxide. However, it is preferable to use them in an amount of 0.5–10% by weight based upon the weight of zirconium oxide.

As for the aldehydes to be used for the raw material of the present invention, n-butyraldehyde, isobutyraldehyde, n-caproic aldehyde, n-octanoic aldehyde and benzaldehyde are illustrated.

It is desirable from the viewpoint of catalyst life that water is present in the reaction, although the reaction proceeds even in the absence of water. As for the amount of water, it is preferable that the molar ratio of water to the sum of aldehyde and carboxylic acid is in the range of 0.1–5.

The reaction proceeds sufficiently about under the atmospheric pressure, but it is also possible to carry out the reaction under a pressure of 0.1–10 atm.

As for the feeding rate of aldehyde plus carboxylic acid, 0.1–30 g/hr per g of catalyst is preferable.

As for the reaction temperature, a temperature in the range of 200°–600°C can be employed, but a temperature in the range of 300°–500°C is practical.

According to the method of the present invention, the catalyst life of two kinds of the catalysts to be used in the present invention is more prolonged and the yield is more improved as compared with the case where a lower aldehyde of 2–3 carbon atoms is used as raw material. These effectivenesses are more achieved in the case where a mixture of zirconium oxide and an alkali metal oxide or an alkaline earth metal oxide is used as catalyst, than in the case where zirconium oxide alone is used as catalyst.

The ketones produced according to the present invention are useful as solvents for rubbers, plastics, etc., reaction solvents, extraction solvents, raw material for various reactions.

The present invention is further illustrated by the following Examples without limiting the scope of claim of the present invention.

EXAMPLE 1

Conc. aqueous ammonia was added to 27% aqueous solution of zirconyl chloride to form a gel-like substance, which was aged over night, followed by repeated filtrations and water-washings, drying at 110°C, and heat-treatment at 300°C for one hour, successively at 600°C for 3 hours. The resulting product was pelletized into pellets of 3 mm × 3 mm by means of a pelletizer. 30 g of zirconium oxide catalyst thus obtained was filled in a silica tube have an inner diameter of 23 mm and a length of 630 mm. Given amounts of acetic acid and isobutyraldehyde, water and nitrogen gas as a carrier, preheated to 350°C, were fed in the reaction tube from one end thereof. The amounts fed to the tube were as follows:

| | |
|---|---|
| Acetic acid | 13.6 g (0.226 mol)/hr |
| Isobutyraldehyde | 18.6 g (0.258 mol)/hr |
| Water | 9.3 g (0.52 mol)/hr |
| Nitrogen gas | 2.4 l/hr |

The reaction temperature was maintained at 450°C. After passing through the reaction tube and a subsequent cooler, a liquid product was obtained. The resulting conversion and selectivity are shown in the following Table:

| | | Conversion (%) | | Selectivity (%) | |
|---|---|---|---|---|---|
| | | Start | After 48 hrs | Start | After 48 hrs |
| Raw material | Acetic acid | 98.3 | 98.5 | — | — |
| | Isobutyraldehyde | 95.1 | 96.0 | — | — |
| Product | Acetone | — | — | 25.1 | 25.3 |
| | Methyl isopropyl ketone | — | — | 33.0 | 33.7 |
| | Diisopropyl ketone | — | — | 35.2 | 37.7 |

COMPARATIVE EXAMPLE 1

Reaction was carried out using acetaldehyde as raw material in place of acetic acid in Example 1.
The amounts fed to the reaction tube were as follows:

| | |
|---|---|
| Acetaldehyde | 11.4 g (0.260 mol)/hr |
| Isobutyraldehyde | 18.6 g (0.258 mol)/hr |
| Water | 9.3 g (0.52 mol)/hr |
| Nitrogen gas | 2.4 l/hr |

The reaction temperature was maintained at 450°C. The results are shown in the following Table:

| | | Conversion (%) | | Selectivity (%) | |
|---|---|---|---|---|---|
| | | Start | After 48 hrs | Start | After 48 hrs |
| Raw material | Acetaldehyde | 98.1 | 57.7 | — | — |
| | Isobutyraldehyde | 95.1 | 43.8 | — | — |
| Product | Acetone | — | — | 22.4 | 20.4 |
| | Methyl isopropyl ketone | — | — | 31.6 | 26.1 |
| | Diisopropyl ketone | — | — | 33.0 | 32.3 |

EXAMPLE 2

Conc. aqueous ammonia was added to 27% aqueous solution of zirconyl chloride, and a shaped catalyst of 3 × 3 mm was obtained in the same manner as in Comparative Example 1. Reaction was carried out using the catalyst under the same conditions as in Example 1, except that propionic acid and n-butyraldehyde were used as raw material.

The amounts fed to the reaction tube were as follows:

| | |
|---|---|
| Propionic acid | 16.6 g (0.225 mol)/hr |
| n-Butyraldehyde | 18.6 g (0.258 mol)/hr |
| Water | 5.6 g (0.312 mol)/hr |
| Nitrogen gas | 2.4 l/hr |

The results are shown in the following Table:

| | | Conversion (%) | | Selectivity (%) | |
|---|---|---|---|---|---|
| | | Start | After 60 hrs | Start | After 60 hrs |
| Raw material | Propionic acid | 97.7 | 97.6 | — | — |
| | n-Butyraldehyde | 97.8 | 97.1 | — | — |
| Product | Diethyl ketone | — | — | 30.1 | 30.0 |
| | Ethyl n-propyl ketone | — | — | 35.3 | 34.9 |
| | Di-n-propyl ketone | — | — | 26.1 | 29.1 |

COMPARATIVE EXAMPLE 2

Reaction was carried out using propionaldehyde in place of propionic acid in Example 2.
The amounts fed to the reaction tube were as follows:

| | |
|---|---|
| Propionaldehyde | 15.0 g (0.259 mol)/hr |
| n-Butyraldehyde | 18.6 g (0.259 mol)/hr |
| Water | 5.6 g (0.312 mol)/hr |
| Nitrogen gas | 2.4 l/hr |

The reaction temperature was 45.0°C. The results are shown in the following Table:

| | | Conversion (%) | | Selectivity (%) | |
|---|---|---|---|---|---|
| | | Start | After 60 hrs | Start | After 60 hrs |
| Raw material | Propionaldehyde | 93.4 | 57.3 | — | — |
| | n-Butyraldehyde | 96.4 | 53.1 | — | — |
| Product | Diethyl ketone | — | — | 30.4 | 23.4 |
| | Ethyl n-propyl ketone | — | — | 30.4 | 30.8 |
| | Di-n-propyl ketone | — | — | 23.5 | 26.1 |

EXAMPLE 3

25% ammonium hydroxide solution was added to 20% aqueous solution of zirconyl nitrate to form a gel-like substance, followed by aging over night, filtration, water washing, drying at 110°C, and heat-treatment at 300°C for one hour, successively at 600°C for 3 hours. The resulting product was pelletized into pellets of 3 mm × 3 mm by means of a pelletizer. 25 g of the resulting zirconyl oxide shaped catalyst was filled in the same reaction tube as in Example 1.

The amounts fed to the reaction tube were as follows:

| | |
|---|---|
| Acetic acid | 15.6 g (0.260 mol)/hr |
| Benzaldehyde | 27.5 g (0.260 mol)/hr |
| Water | 5.6 g (0.312 mol)/hr |
| Nitrogen gas | 2.4 l/hr |

The reaction temperature was maintained at 480°C.

The results are shown in the following Table:

| | | Conversion(%) | | Selectivity(%) | |
|---|---|---|---|---|---|
| | | Start | After 50 hrs | Start | After 50 hrs |
| Raw material | Acetic acid | 97.6 | 96.1 | — | — |
| | Benzaldehyde | 93.3 | 92.3 | — | — |
| Product | Acetone | — | — | 27.7 | 28.1 |
| | Acetophenone | — | — | 30.4 | 30.1 |
| | Benzophenone | — | — | 27.1 | 28.4 |

COMPARATIVE EXAMPLE 3

Acetaldehyde was used as raw material at a feeding rate of 11.4 g (0.260 mol)/hr in place of acetic acid in Example 3. Other reaction conditions were maintained in the same manner. The results are shown in the following Table:

| | | Conversion(%) | | Selectivity(%) | |
|---|---|---|---|---|---|
| | | Start | After 50 hrs | Start | After 50 hrs |
| Raw material | Acetaldehyde | 98.4 | 50.3 | — | — |
| | Benzaldehyde | 91.4 | 48.3 | — | — |
| Product | Acetone | — | — | 30.4 | 27.1 |
| | Acetophenone | — | — | 28.4 | 25.1 |
| | Benzophenone | — | — | 28.3 | 28.4 |

EXAMPLE 4

Acetic acid was reacted with n-caproic aldehyde using the same catalyst and the same apparatus as in Example 3.

The amounts fed to the reaction tube were as follows:

| n-Caproic aldehyde | 20 g (0.116 mol)/hr |
| Acetic acid | 6 g (0.10 mol)/hr |
| Water | 4 g/hr |
| Nitrogen gas | 2.4 l/hr |

The reaction temperature was maintained at 460°C. The results of reaction were as follows:

| | | Conversion(%) | | Selectivity(%) | |
|---|---|---|---|---|---|
| | | Start | After 48 hrs | Start | After 48 hrs |
| Raw material | Acetic acid | 98.4 | 97.7 | — | — |
| | n-Caproic aldehyde | 93.4 | 94.1 | — | — |
| Product | Acetone | — | — | 20.3 | 20.0 |
| | Methyl amyl ketone | — | — | 34.1 | 33.1 |
| | Diamyl ketone | — | — | 34.1 | 34.1 |

COMPARATIVE EXAMPLE 4

Example 4 was repeated except that acetaldehyde was used at a feeding rate of 4.4 g (0.10 mol)/hr in place of acetic acid. Other reaction conditions were maintained in the same manner. The results were as follows:

| | | Conversion(%) | | Selectivity(%) | |
|---|---|---|---|---|---|
| | | Start | After 48 hrs | Start | After 48 hrs |
| Raw material | Acetaldehyde | 98.4 | 60.1 | — | — |
| | n-Caproic aldehyde | 94.3 | 50.4 | — | — |
| Product | Acetone | — | — | 19.3 | 16.1 |
| | Methyl amyl ketone | — | — | 30.4 | 28.8 |
| | Diamyl ketone | — | — | 32.1 | 35.0 |

EXAMPLE 5

25% ammonium hydroxide solution was added to 20% aqueous solution of zirconyl nitrate to form a gel-like substance, followed by aging over night, filtration, water washing, drying at 110°C, and heat treatment at 300°C for one hour, successively at 600°C for 3 hours. The resulting product was pelletized into pellets of 3 mm × 3 mm by means of a pelletized. 30 g of the resulting zirconium oxide shaped catalyst was filled in a reaction tube of silica (inner diameter: 23 mm. length 630 mm). The following materials preheated to 350°C were fed to the tube:

| Acetic acid | 6.4 g (0.106 mol)/hr |
| n-Octanoic aldehyde | 23.6 g (0.118 mol)/hr |
| Water | 5.4 g (0.3 mol)/hr |
| Nitrogen gas | 2.4 l/hr |

The results of the reaction at 460°C were as follows:

| | | Conversion (%) | | Selectivity (%) | |
|---|---|---|---|---|---|
| | | Start | After 70 hrs | Start | After 70 hrs |
| Raw material | Acetic acid | 97.3 | 93.1 | — | — |
| | n-Octanoic aldehyde | 95.4 | 94.1 | — | — |
| Product | Acetone | — | — | 19.3 | 17.1 |
| | Methyl hexyl ketone | — | — | 33.9 | 34.1 |
| | Dihexyl ketone | — | — | 30.4 | 35.4 |

COMPARATIVE EXAMPLE 5

Example 5 was repeated except that acetaldehyde was used at a feeding rate of 4.7 g (0.106 mol)/hr in place of acetic acid. The results were as follows:

| | | Conversion (%) | | Selectivity(%) | |
|---|---|---|---|---|---|
| | | Start | After 68 hrs | Start | After 68 hrs |
| Raw material | Acetaldehyde | 97.7 | 50.0 | — | — |
| | n-Caproic aldehyde | 94.1 | 44.4 | — | — |
| Product | Acetone | — | — | 17.3 | 16.4 |
| | Methyl hexyl ketone | — | — | 33.1 | 30.6 |
| | Dihexyl ketone | — | — | 30.4 | 33.1 |

EXAMPLE 6

Magnesium nitrate was added to 27% aqueous solution of zirconyl chloride, in an atomic ratio of Mg/Zr of 0.02 to form a solution. Conc. aqueous ammonia was added to the resulting solution to form a gel-like substance, followed by aging over night, repeated filtrations and water washings, drying at 110°C, and heat-treatment at 300°C for one hour, successively at 600°C for 3 hours. The resulting product was pelletized into pellets of 3 mm × 3 mm by means of a pelletizer. 30 g of the resulting zirconium oxide-magnesium oxide catalyst was filled in a silica tube (inner diameter: 23 mm, length: 630 mm). Given amounts of acetic acid, isobutyraldehyde, water and nitrogen gas as carrier, preheated to 350°C, were fed into the reaction tube from one end thereof.

The amounts fed to the tube were as follows:

| | |
|---|---|
| Acetic acid | 13.6 g (0.226 mol)/hr |
| Isobutyraldehyde | 18.6 g (0.258 mol)/hr |
| Water | 9.3 g (0.52 mol)/hr |
| Nitrogen gas | 2.4 l/hr |

The reaction temperature was maintained at 450°C. After passing through the reaction tube and a subsequent cooler, a liquid product was obtained. The resulting conversion and selectivity were as follows:

| | | Conversion(%) | | Selectivity(%) | |
|---|---|---|---|---|---|
| | | Start | After 48 hrs | Start | After 48 hrs |
| Raw material | Acetic acid | 99.5 | 99.3 | — | — |
| | Iso-butyraldehyde | 95.6 | 96.2 | — | — |
| Product | Acetone | — | — | 26.3 | 25.8 |
| | Methyl isopropyl ketone | — | — | 33.2 | 34.1 |
| | Diisopropyl ketone | — | — | 35.1 | 37.4 |

COMPARATIVE EXAMPLE 6

Reaction was carried out using acetaldehyde as raw material in place of acetic acid in Example 6.
The amounts fed to the reaction tube were as follows:

| | |
|---|---|
| Acetaldehyde | 11.4 g (0.260 mol)/hr |
| Isobutyraldehyde | 18.6 g (0.258 mol)/hr |
| Water | 9.3 g (0.52 mol)/hr |
| Nitrogen gas | 2.4 l/hr |

The reaction temperature was maintained at 450°C. The results were as follows:

| | | Conversion (%) | | Selectivity(%) | |
|---|---|---|---|---|---|
| | | Start | After 48 hrs | Start | After 48 hrs |
| Raw Material | Acetaldehyde | 98.8 | 58.7 | — | — |
| | Iso-butyraldehyde | 96.9 | 47.3 | — | — |
| Product | Acetone | — | — | 23.1 | 20.8 |
| | Methyl isopropyl ketone | — | — | 31.8 | 28.7 |
| | Diisopropyl ketone | — | — | 33.1 | 30.3 |

EXAMPLE 7

Magnesium nitrate and potassium nitrate were added to 27% aqueous solution of zirconyl chloride so as to give an atomic ratio of Zr:Mg:K of 94.2:4.0:1.8, and dissolved. Conc. aqueous ammonia was added to the resulting solution, and a shaped catalyst of 3 mm × 3 mm in the same manner as in Comparative Example 6. Reaction was carried out using the catalyst, under the same conditions as in Example 6, except that propionic acid and n-butyraldehyde were used as raw materials.

The amounts fed to the reaction tube were as follows:

| | |
|---|---|
| Propionic acid | 16.6 g (0.225 mol)/hr |
| n-Butyraldehyde | 18.6 g (0.258 mol)/hr |
| Water | 5.6 g (0.312 mol)/hr |
| Nitrogen gas | 2.4 l/hr |

The results are shown in the following Table:

| | | Conversion(%) | | Selectivity(%) | |
|---|---|---|---|---|---|
| | | Start | After 60 hrs | Start | After 60 hrs |
| Raw material | Propionic acid | 98.8 | 98.7 | — | — |
| | n-Butyraldehyde | 97.9 | 98.0 | — | — |
| Product | Diethyl ketone | — | — | 32.3 | 32.4 |
| | Ethyl n-propyl ketone | — | — | 36.1 | 36.0 |
| | Di-n-propyl ketone | — | — | 23.3 | 25.1 |

COMPARATIVE EXAMPLE 7

Reaction was carried out using propionaldehyde in place of propionic acid in Example 7.
The amounts fed to the reaction tube were as follows:

| | |
|---|---|
| Propionaldehyde | 15.0 g (0.259 mol)/hr |
| n-butyraldehyde | 18.6 g (0.259 mol)/hr |
| Water | 5.6 g (0.312 mol)/hr |
| Nitrogen gas | 2.4 l/hr |

The reaction temperature was 450°C. The results were as follows:

| | | Conversion (%) | | Selectivity (%) | |
|---|---|---|---|---|---|
| | | Start | After 60 hrs | Start | After 60 hrs |
| Raw material | Propionaldehyde | 97.7 | 61.3 | — | — |
| | n-Butyraldehyde | 97.1 | 57.0 | — | — |
| Product | Diethyl ketone | — | — | 30.3 | 28.1 |
| | Ethyl n-propyl ketone | — | — | 32.1 | 30.8 |
| | Di-n-propyl ketone | — | — | 25.1 | 23.3 |

EXAMPLE 8

25% ammonium hydroxide solution was added to 20% aqueous solution of zirconyl nitrate to form a gel-like substance, followed by aging over night, filtration, water washing, drying at 110°C, and heat-treatment at 300°C for one hour, successively at 600°C for 3 hours. The resulting product was pelletized into pellets of 3 mm × 3 mm by means of a pelletizer. The resulting zirconium oxide shaped catalyst was dipped in 3% aqueous solution of lithium nitrate over night, followed by filtration, drying at 110°C, and heat-treatment at 300°C for one hour, successively at 600°C for 3 hours. The supported amount of LiO was 2% by weight. 25 g of the resulting catalyst was filled in the same reaction tube as in Example 6.

The amounts fed to the reaction tube were as follows:

| | |
|---|---|
| Acetic acid | 15.6 g (0.260 mol)/hr |
| Benzaldehyde | 27.5 g (0.260 mol)/hr |
| Water | 5.6 g (0.312 mol)/hr |
| Nitrogen gas | 2.4 l/hr |

The reaction temperature was maintained at 480°C. The reaction results were as follows:

| | | Conversion (%) | | Selectivity(%) | |
|---|---|---|---|---|---|
| | | Start | After 50 hrs | Start | After 50 hrs |
| Raw material | Acetic acid | 98.7 | 98.8 | — | — |
| | Benzaldehyde | 94.4 | 94.8 | — | — |
| Product | Acetone | — | — | 28.8 | 30.5 |
| | Acetophenone | — | — | 33.1 | 32.9 |
| | Benzophenone | — | — | 29.3 | 28.8 |

COMPARATIVE EXAMPLE 8

Acetaldehyde was used at a feeding rate of 11.4 g (0.260 mol)/hr in place of acetic acid in Example 8. Other reaction conditions were maintained in the same manner. The results were as follows:

| | | Conversion(%) | | Selectivity(%) | |
|---|---|---|---|---|---|
| | | Start | After 50 hrs | Start | After 50 hrs |
| Raw material | Acetaldehyde | 98.8 | 55.7 | — | — |
| | Benzaldehyde | 93.2 | 50.3 | — | — |
| Product | Acetone | — | — | 30.2 | 29.7 |
| | Acetophenone | — | — | 29.5 | 27.2 |
| | Benzophenone | — | — | 28.3 | 28.5 |

EXAMPLE 9

Acetic acid was reacted with n-caproic aldehyde using the same catalyst and apparatus as in Example 8. The amounts fed to the reaction tube were as follows:

| | | |
|---|---|---|
| n-caproic aldehyde | 20 | g (0.116 mol)/hr |
| Acetic acid | 6.0 | g (0.10 mol)/hr |
| Water | 4 | g (0.222 mol)/hr |
| Nitrogen gas | 2.4 | l/hr |

The reaction temperature was maintained at 460°C. The reaction results were as follows:

| | | Conversion(%) | | Selectivity(%) | |
|---|---|---|---|---|---|
| | | Start | After 48 hrs | Start | After 48 hrs |
| Raw material | Acetic acid | 99.8 | 98.7 | — | — |
| | n-Caproic aldehyde | 95.1 | 94.5 | — | — |
| Product | Acetone | — | — | 22.5 | 20.1 |
| | Methyl amyl ketone | — | — | 35.1 | 34.1 |
| | Diamyl ketone | — | — | 35.3 | 33.3 |

COMPARATIVE EXAMPLE 9

Example 9 was repeated except that acetaldehyde was used at a feeding rate of 4.4 g (0.10 mol)/hr in place of acetic acid. The results were as follows:

| | | Conversion(%) | | Selectivity(%) | |
|---|---|---|---|---|---|
| | | Start | After 48 hrs | Start | After 48 hrs |
| Raw material | Acetaldehyde | 99.3 | 60.5 | — | — |
| | n-Capronaldehyde | 95.3 | 51.3 | — | — |
| Product | Acetone | — | — | 20.1 | 17.3 |
| | Methyl amyl ketone | — | — | 33.1 | 30.0 |
| | Diamyl ketone | — | — | 32.1 | 34.1 |

EXAMPLE 10

25% ammonium hydroxide solution was added to 20% aqueous solution of zirconyl nitrate to form a gel-like substance, followed by aging over night, filtration, water-washing, drying at 110°C, and heat-treatment at 300°C for one hour, successively at 600°C for 3 hours. The resulting product was pelletized into pellets of 3 mm × 3 mm by means of a pelletizer.

The resulting zirconium oxide shaped catalyst was dipped in 3% aqueous solution of sodium nitrate over night, followed by filtration, drying at 110°C, and heat-treatment at 300°C for one hour, successively at 600°C for 3 hours. The supported amount of Na$_2$O was 2.2 percent. 30 g of the resulting catalyst was filled in a reaction tube of silica (inner diameter: 23 mm, length 163 mm). The following materials preheated to 350°C were fed to the tube:

| | | |
|---|---|---|
| Acetic acid | 6.4 | g (0.106 mol)/hr |
| n-Octanoic aldehyde | 23.6 | g (0.118 mol)/hr |
| Water | 5.4 | g (0.3 mol)/hr |
| Nitrogen gas | 2.4 | l/hr |

The results of the reaction at 460°C were as follows:

| | | Conversion(%) | | Selectivity(%) | |
|---|---|---|---|---|---|
| | | Start | After 70 hrs | Start | After 70 hrs |
| Raw material | Acetic acid | 98.7 | 98.3 | — | — |
| | n-Octanoic aldehyde | 96.1 | 95.7 | — | — |
| Product | Acetone | — | — | 20.3 | 19.5 |
| | Methyl hexyl ketone | — | — | 35.3 | 35.1 |
| | Dihexyl ketone | — | — | 33.2 | 32.7 |

COMPARATIVE EXAMPLE 10

Example 10 was repeated except that acetaldehyde was used at a feeding rate of 4.7 g (0.106 mol)/hr in place of acetic acid. The results were as follows:

| | | Conversion(%) | | Selectivity(%) | |
|---|---|---|---|---|---|
| | | Start | After 68 hrs | Start | After 68 hrs |
| Raw material | Acetaldehyde | 98.1 | 50.3 | — | — |
| | n-Caproic aldehyde | 95.5 | 48.8 | — | — |
| | Acetone | — | — | 19.1 | 17.3 |

-continued

|  |  | Conversion(%) | | Selectivity(%) | |
| --- | --- | --- | --- | --- | --- |
|  |  | Start | After 68 hrs | Start | After 68 hrs |
| Product | Methyl hexyl ketone | — | — | 34.1 | 33.5 |
|  | Dihexyl ketone | — | — | 30.3 | 32.5 |

What is claimed is:

1. A method for producing ketones which comprises reacting an aldehyde selected from the group consisting of straight chain or branched chain aliphatic aldehydes having a carbon atom number of 4 to 10 (inclusive) with a monocarboxylic acid selected from the group consisting of acetic acid and propionic acid in the presence of water and zirconium oxide at a temperature in the range of 200° to 600°C.

2. A method according to claim 1 wherein said aliphatic aldehydes are n-butyraldehyde, isobutyraldehyde, n-caproic aldehyde and n-octanoic aldehyde.

3. A method according to claim 1 wherein said temperature is in the range of 300°–500°C.

4. A method according to claim 1 wherein the feeding rates of said aldehyde and said monocarboxylic acid are in the range of 0.1–30 g/hr, respectively.

5. A method for producing ketones which comprises reacting an aldehyde selected from the group consisting of straight chain or branched chain aliphatic aldehydes having a carbon atom number of 4 to 10 (inclusive) with a monocarboxylic acid selected from the group consisting of acetic acid and propionic acid in the presence of water and a mixture of 99.5 to 90% by weight of zirconium oxide and 0.5 to 10% by weight of at least one metal oxide selected from the group consisting of alkali metal oxides and alkaline earth metal oxides, at a temperature in the range of 200° to 600°C.

6. A method according to claim 5 wherein said alkali metal oxides are oxides of Li, K and Mg.

7. A method according to claim 5 wherein said aliphatic aldehydes are n-butyraldehyde isobutyraldehyde, n-caproic aldehyde and n-octanoic aldehyde.

8. A method according to claim 5 wherein said temperature is in the range of 300°–500°C.

9. A method according to claim 5 wherein the feeding rates of said aldehyde and said monocarboxylic acid are in the range of 0.1–30 g/hr, respectively.

10. A method according to claim 1 wherein said water is in a molar ratio of 0.15–5 relative to the molar sum of aldehyde and carboxylic acid.

11. A method according to claim 5 wherein said water is in a molar ratio of 0.15–5 relative to the molar sum of aldehyde and carboxylic acid.

* * * * *